United States Patent [19]
Sachse

[11] Patent Number: 5,591,145
[45] Date of Patent: Jan. 7, 1997

[54] CATHETER WITH WALL PERFORATIONS

[76] Inventor: Hans-Ernst Sachse, Lerchenstrasse 55, 90425 Nuernberg, Germany

[21] Appl. No.: 510,567

[22] Filed: Aug. 2, 1995

[51] Int. Cl.$^6$ ...................................................... A61F 5/44
[52] U.S. Cl. .......................... 604/349; 604/328; 604/317; 604/96
[58] Field of Search .............................. 604/174, 43–45, 604/96, 99–103, 335, 349, 317, 328

[56] References Cited

U.S. PATENT DOCUMENTS

| | | | |
|---|---|---|---|
| 4,501,580 | 2/1985 | Glassman | 604/43 |
| 4,610,660 | 9/1986 | Rosenberg | 604/49 |
| 4,878,901 | 11/1989 | Sachse | 604/174 |

FOREIGN PATENT DOCUMENTS

| | | | |
|---|---|---|---|
| 3306342 | 8/1984 | Germany | A61M 25/00 |

Primary Examiner—Randall L. Green
Assistant Examiner—Perry E. Van Over
Attorney, Agent, or Firm— Keil & Weinkauf

[57] ABSTRACT

A urethral catheter designed to employ the principle of urethral irrigation with the patient's own urine to combat rising infection. This irrigation is achieved by having the section of the catheter which lies in the urethra equipped with windows which are arranged so that large surface areas of the urethral mucous membranes are irrigated by urine. Through judicious positioning of a mandrin in the catheter's lumen one can achieve a forced flow of urine through these windows and between the catheter and the urethral mucous membranes, the flow returning through further windows into the hollow interior of the mandrin and proceeding out of the body to a drainage system.

10 Claims, 6 Drawing Sheets

CATHETER WITH WALL PERFORATIONS

This invention mimics the body's own defense against infection of the urethra through irrigation of the urethral mucosa with urine. This object is shared by German applications DE 32 02 713 C2, DE 33 06 342 A1, DE 36 34 569.5 and G 86 26 896.1. In the instant invention the wall of the catheter contains one or more openings or windows (9) where it passes through the urethra. The urine passing through the interior of the catheter can flow through these relatively large windows to the surrounding mucosa of the urethra and irrigate them. Compared with the cited applications, the catheter of the instant invention can be constructed relatively simply and inexpensively. While the wall openings of P 33 06 342 primarily serve to lead urine from the area between the urethral wall and the catheter wall back into the lumen of the catheter, in the instant invention the urine circulates from the lumen through the windows outward towards the urethral wall—i.e. in the opposite direction—and back to the lumen. Through this continual irrigation of the numerous urethral areas, bacteria ascending from the orifice of the urethra are rinsed away.

In one variation adjacent windows (9) are staggered in their locations relative to each other, as shown in FIG. 4. In order, if required, to ensure sufficient stiffness of the catheter wall in the region of the windows, the catheter wall material in this region may be made stiffer than in the remaining parts of the catheter, so as to hold the catheter lumen (18) open. A preferred way to keep the catheter from being expelled from the bladder is through the use of a balloon (3), as shown in FIGS. 1–3. The inflation channel (4) for such a balloon (3) is, in the window-equipped region of the catheter, routed within the lumen, so as not to interfere with the windows. In a variation on this embodiment, the inflation channel (4) is integrated into the catheter wall, itself. In an especially preferred embodiment, the urine is routed between the outside surface of the catheter wall and the mucosa of the urethra by means of a hollow mandrin (19) appropriately placed in the lumen (18) of the catheter, the mandrin thereby blocking off the lumen of the catheter. The urine continues to flow in this manner until it encounters an opening (20) in the mandrin which permits the urine to flow into and through the lumen of the hollow mandrin. In a variation on this last embodiment the mandrin (19) possesses a narrower central section (23), which permits, in that area, some urine flow between the outer surface of the mandrin (19) and the inner surface of the catheter wall (1), in order to optimize the irrigating effect. In a further embodiment of this invention, a sealing ring (22), located after the farthest window from the bladder, prevents the urine from flowing past it between the catheter wall and the mucousa of the urethra to the beginning of the urethra. As mentioned above, the catheter tip (2) can be retained in the bladder through inflation of a balloon (3), as shown in FIGS. 1–3. On the other hand, other retention means may also be employed, such as the "Casper-tip" shown in FIG. 5, or those according to Pezzer and Malecot (not depicted).

Other features and advantages of the invention are discussed in the further description and the drawings, as well as in the subclaims.

DESCRIPTION OF THE PREFERRED EMBODIMENTS

Figure 1:
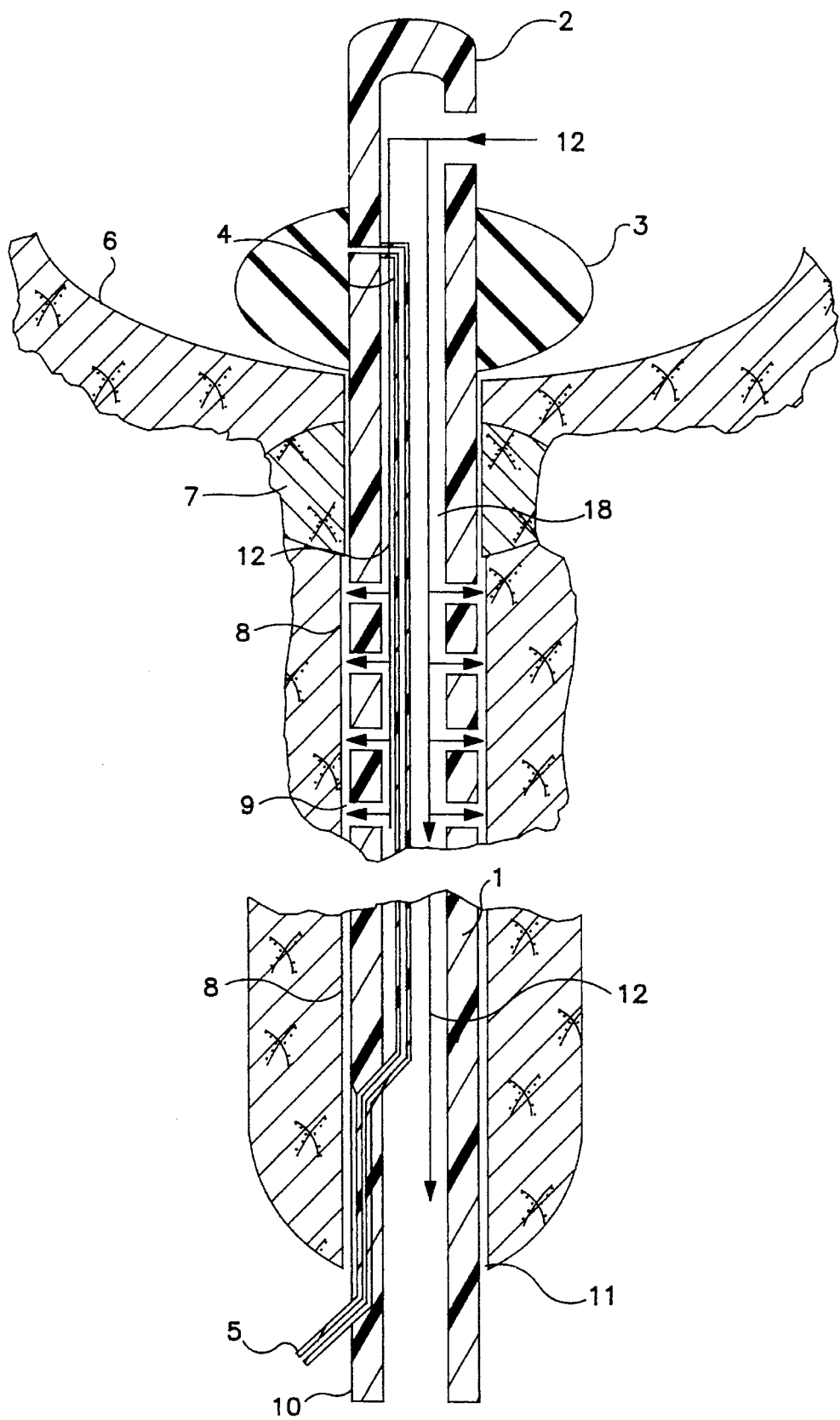
FIG. 1 a first embodiment of the invention shown in longitudinal cross-section of the catheter located in the bladder and urethra.

According to the embodiment depicted in FIG. 1, the tip (2) of the catheter is held in the bladder by a balloon (3) which, once tip and balloon are introduced into the bladder, is inflated with air or liquid through the inflation channel (4). The inflation channel (4) can lie largely unsecured in the lumen (18) of the catheter, ultimately passing through the wall (1) of the catheter to connect to the inflation tap (5). Where it passes through the urethra, the catheter wall (1) is provided with windows (9). The urine can flow through these windows in the direction indicated by reference numeral 12, and thereby irrigate the urethral mucous membranes.

Figure 2:
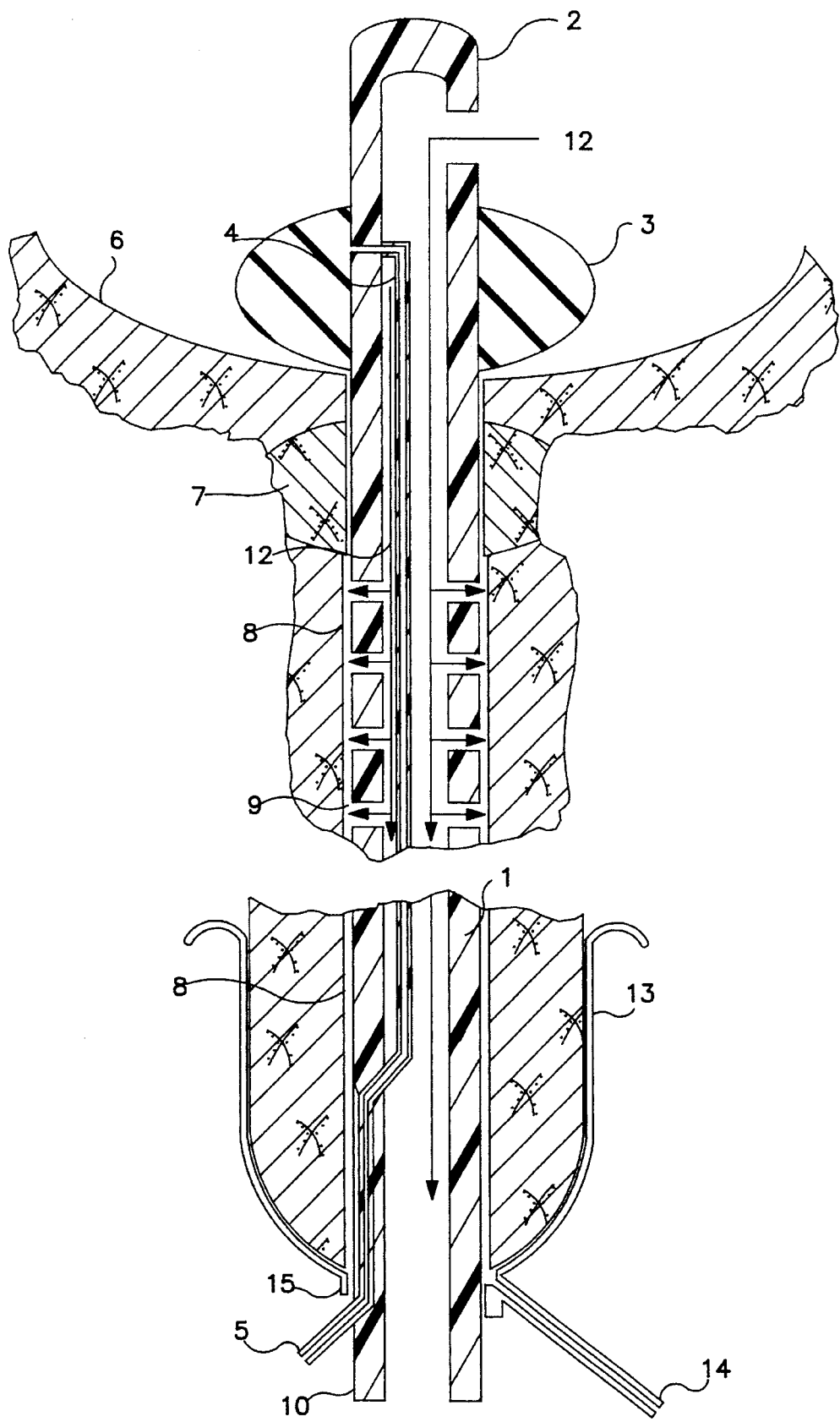
FIG. 2 another embodiment of the invention with a condom urinal, in longitudinal cross-section FIG. 3 the catheter in plan view FIG. 4 a portion of the window-equipped region of the catheter in plan view FIG. 5 longitudinal cross-section of a catheter with a "Casper-tip" and a mandrin FIG. 6 longitudinal cross-section of a catheter with a "Casper-tip" and a mandrin, the latter having a narrower central section

In the embodiment depicted in FIG. 2 the small quantity of which manages to flow toward the outside of the body between the urethral mucous membranes and the catheter wall is captured by a condom urinal (13), and flows through the drain tap (14) to a not-depicted drainage system.

Figure 3:
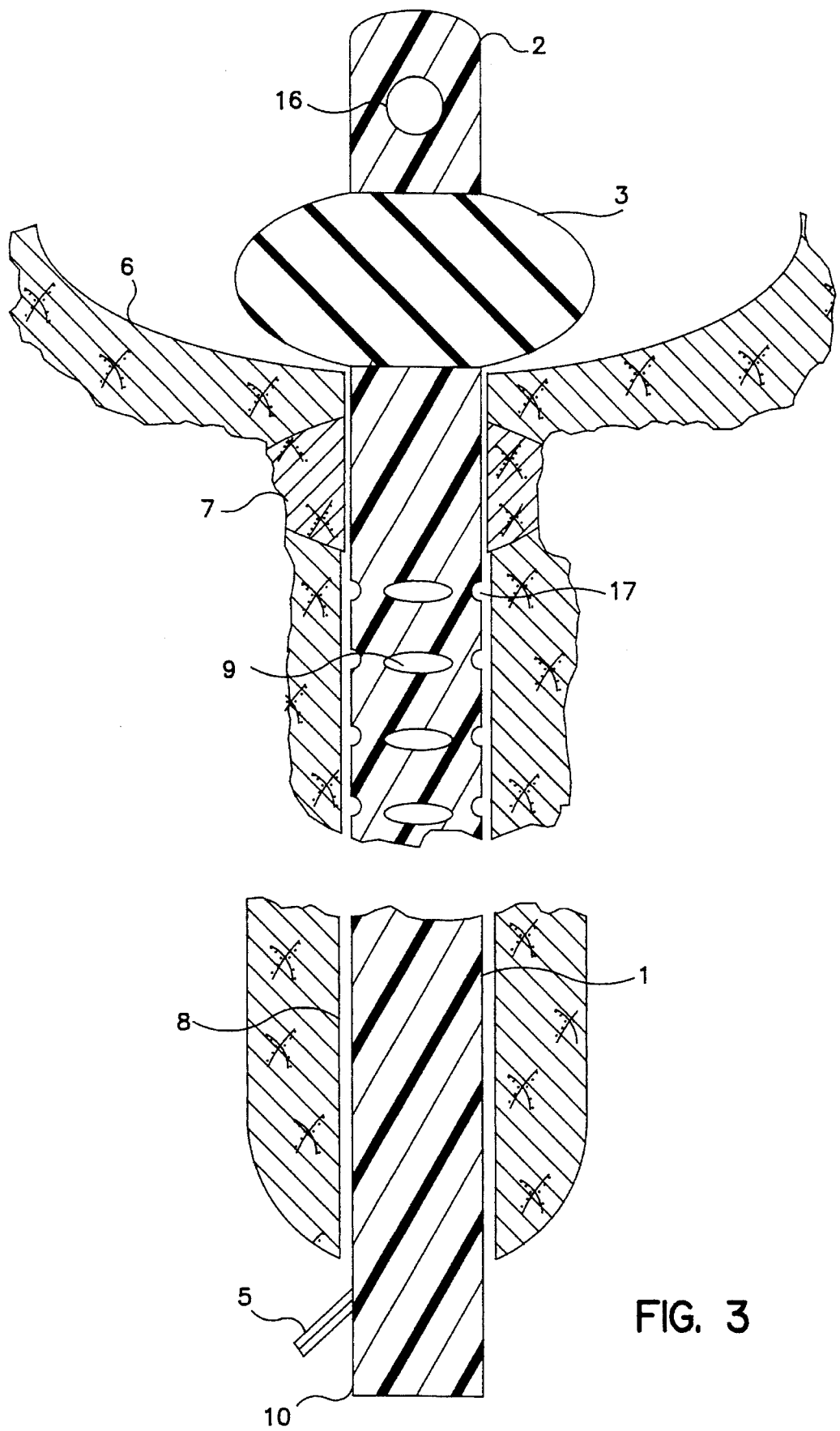

FIG. 3 is a plan view of the catheter, showing windows (9) arranged in rows against a cross-section of the bladder and urethral regions.

Figure 4:
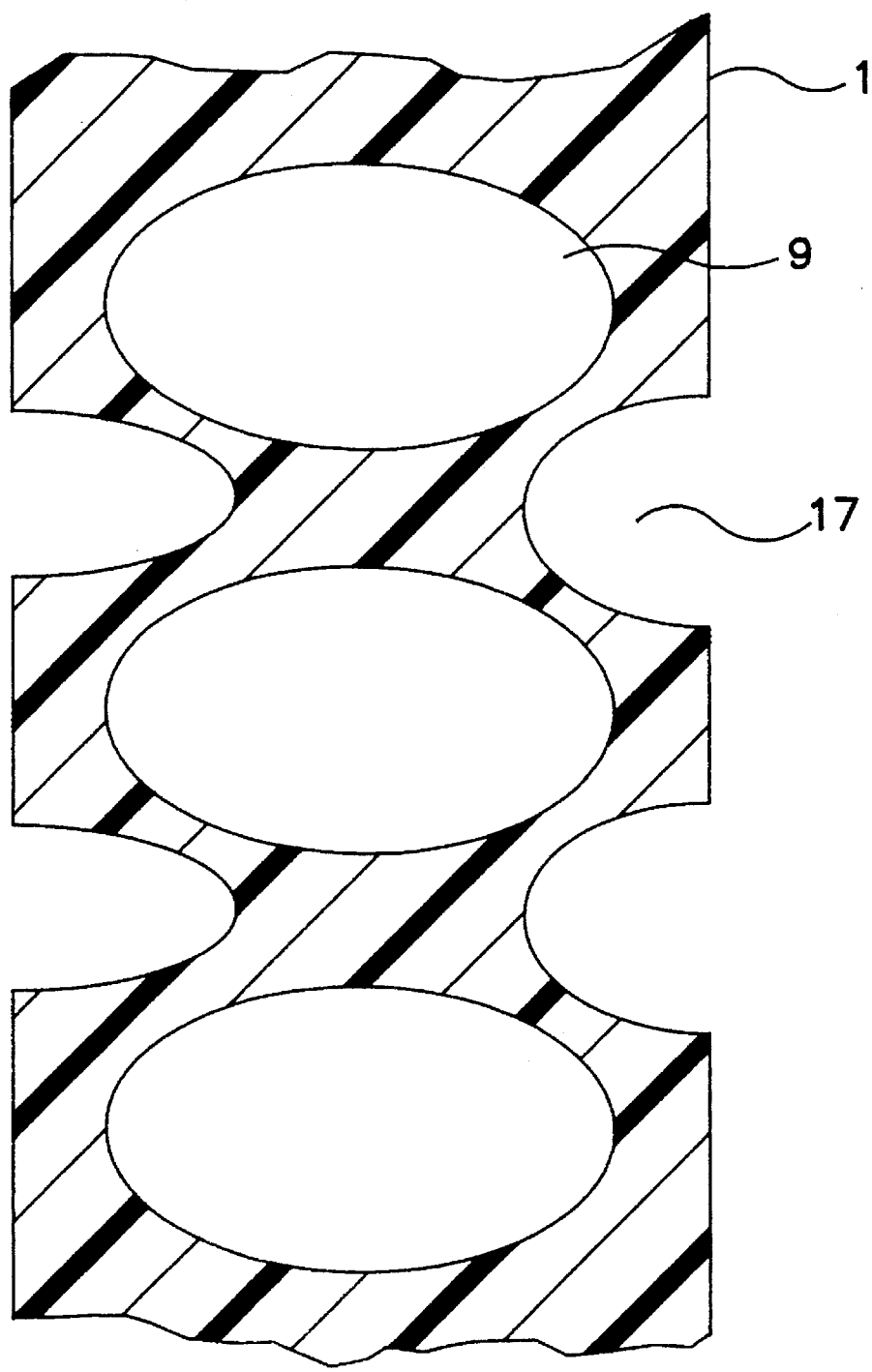

FIG. 4 shows a window-equipped section of the catheter with longitudinal rows of relatively large windows which would overlap each other, were neighboring rows not staggered. Due to the size of the windows, the catheter wall here is significantly weakened, and is therefore preferably made of a stronger material in this region.

Figure 5:
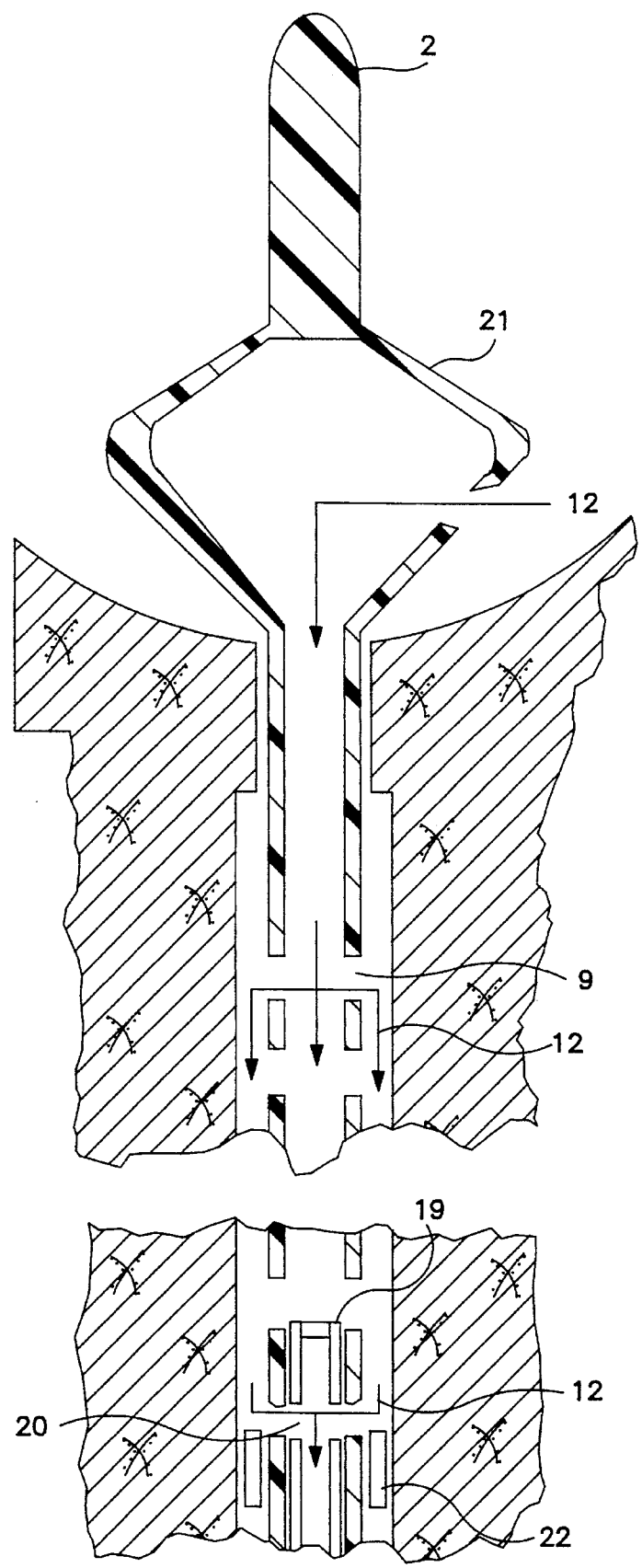

In the embodiment depicted in FIG. 5 a hollow mandrin (19) is shown in longitudinal cross-section. The tip of this hollow mandrin is closed, but some millimeters from the tip the mandrin's wall has one or more openings into the mandrin's lumen. As shown in FIG. 5 the hollow mandrin (19) can be positioned in the catheter lumen (18) in such a way that the mandrin's closed tip blocks off the catheter lumen (18) between the catheter lumen's penultimate and last windows. In this way the urine is forced, at least in this area, to flow between the windowed catheter wall and the wall of the urethra. The urine can return to the catheter lumen through the last window, passing from there into the mandrin lumen through the mandrin opening (20), and thence flowing through the mandrin lumen to a disposal system (not shown).

Figure 6:
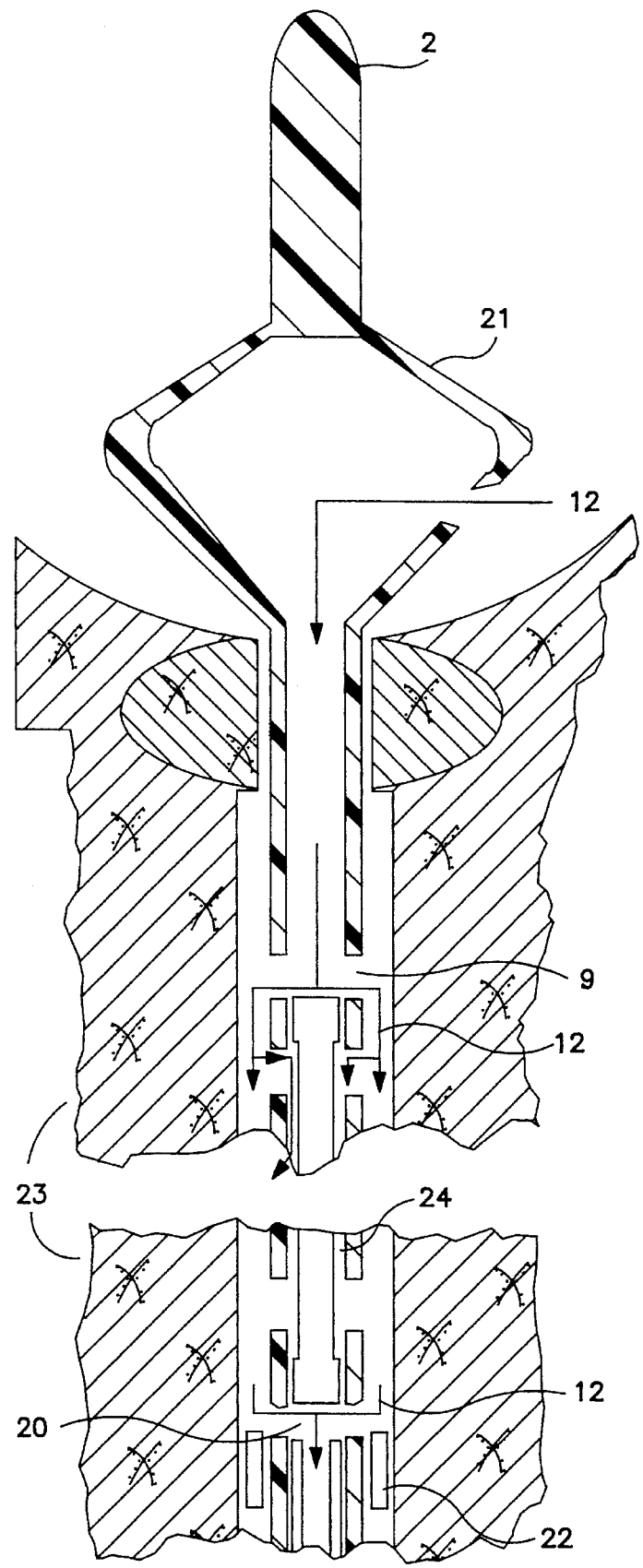

If the mandrin is equipped with a tip capable of blocking the catheter lumen, with this tip followed by a narrower central section in the region of the windows, and the tip of the mandrin in positioned in the vicinity of the first window, then, as shown in FIG. 6, the urine flow will irrigate both the urethral mucous membranes as well as the interior of the catheter wall. In an embodiment without this narrower central section (not shown) the irrigate would be restricted to the urethral mucosa and the exterior of the catheter wall.

Adjacent to the last window, i.e. the one closest to the orifice of the urethra, but just beyond it, i.e. closer to the orifice of the urethra, there is a sealing ring (22), preferably made of a foam-like material, which may contain a substance with oligodynamic properties.

Index to Reference Numerals 1. catheter wall
2. catheter tip
3. balloon
4. inflation channel for the balloon
5. inflation tap for the inflation channel
6. inner wall of the bladder
7. prostate/sphincter region
8. urethral wall/mucous membranes
9. [catheter wall] window
10. catheter end
11. tip of penis
12. direction of urine flow
13. wall of the condom catheter
14. condom catheter drain tap
15. condom sleeve
16. urine entry opening of the catheter (plan view)
17. window of the catheter wall (side view)
18. catheter lumen
19. mandrin
20. mandrin opening
21. "Casper tip" of catheter
22. sealing ring
23. narrower central section of the mandrin
24. space between the inner surface of the catheter and the outer wall of the mandrin

I claim:

1. A catheter for implantation in a bladder and urethra comprising a body having a lumen, said body having a first end and an opposite end and an inner wall and an outer wall,
   means adjacent to the opposite end of the body for preventing expulsion from the bladder;
   one or more windows in an area located between the first end and the opposite end, said windows interconnecting said inner wall and other wall of the body, said catheter being comprised of a material which is stiffer in the area where its windows are located than in the remainder of the catheter and;
   wherein the windows are adjacent to the walls of the urethra when installed in the patient and permit circulation of the urine from the lumen through the windows toward the urethral walls and back to the lumen.

2. A catheter as defined in claim 1, wherein the windows are staggered in relation to each other, and can be of various shapes.

3. A catheter as defined in claim 1, wherein the means for preventing the expulsion of the catheter from the bladder is a balloon, which balloon is inflated via a balloon inflation channel, which balloon inflation channel is located, in the area of the catheter's windows, in the lumen of the catheter.

4. A catheter as defined in claim 1, wherein the means for preventing the expulsion of the catheter from the bladder is a balloon, which balloon is inflated via a balloon inflation channel, which balloon inflation channel is located in the wall of the catheter.

5. A catheter as defined in claim 1, wherein a hollow mandrin is provided in the catheter lumen, said mandrin shaped and located in such a way as to have, opposite the farthest catheter window relative to the bladder, an opening leading to the hollow interior of the mandrin, said mandrin further shaped and located in such a way as to block off the catheter lumen just towards the bladder from said farthest catheter window.

6. A catheter as defined in claim 1, having: a mandrin with a tip sized for blocking off the catheter lumen, and a narrower central section which permits a gap between the mandrin and the catheter wall in this central section.

7. A catheter as defined in claim 1, wherein the exterior of the catheter wall is equipped with a sealing ring, located just beyond the farthest window from the bladder.

8. A catheter as defined in claim 7, wherein the sealing ring contains a substance having an oligodynamic effect, or is made from metal having an oligodynamic effect.

9. A catheter as defined in claim 5, wherein the ends of the mandrin and the catheter can be joined or screwed to one another.

10. A catheter as defined in claim 6, wherein the ends of the mandrin and the catheter can be joined or screwed to one another.

* * * * *